United States Patent [19]

Plummer

[11] Patent Number: 4,837,307

[45] Date of Patent: Jun. 6, 1989

[54] [1,1'-BIPHENYL]COMPOUNDS HAVING A 2,2'-(ALKYL)BRIDGE AND A 3-YL(SUBSTITUTED)METHYL SUBSTITUENT

[75] Inventor: Ernest L. Plummer, Yardley, Pa.

[73] Assignee: FMC Corporation, Philadelphia, Pa.

[21] Appl. No.: 571,250

[22] Filed: Jan. 16, 1984

Related U.S. Application Data

[60] Continuation-in-part of Ser. No. 331,506, Dec. 17, 1981, Pat. No. 4,433,182, which is a division of Ser. No. 259,111, Apr. 30, 1981, abandoned.

[51] Int. Cl.$^4$ ............... C07C 113/02; C07C 143/72; C07C 143/78; C07C 87/30

[52] U.S. Cl. .................... 534/563; 558/53; 558/54; 558/56; 558/57; 558/58; 546/347; 548/480; 564/82; 564/87; 564/90; 564/282; 564/387; 568/808

[58] Field of Search .................. 568/808; 260/141; 534/563; 558/53, 54, 56, 57, 58; 546/347; 564/82, 87, 90, 282, 387

[56] References Cited

PUBLICATIONS

Anet et al., Chemical Abstracts, vol. 51, cols. 2695, 2696 (1957).
Backmann, J. Amer. Chem. Soc., vol. 57, pp. 1381 and 1382 (1935).
Braun et al., Ber Deut Gem. Gesell, vol. 57, pp. 191 to 194 (1924).
Cioranescu et al., Chemical Abstracts, vol. 62, col. 6358d (1965).
Cram et al., "Organic Chemistry", Second edition, p. 274 (1964).
Fierens et al., Chemical Abstracts, vol. 50, cols. 10069a,e (1956).
Johnson et al., J. Amer. Chem. Soc., vol. 83, pp. 417 to 423 (1961).
Miles Lab., Chemical Abstracts, vol. 49, cols. 5530e,f (1955.
Morrison I, Chemical Abstracts, vol. 53, cols. 21831 to 21832 (1959).
Morrison II, Chemical Abstracts, vol. 55, cols. 14401f,h (1961).
Mosettig et al., J. Amer. Chem. Soc., vol. 55, pp. 2995 to 2999 (1933).
Pinck et al., J. Amer. Chem. Soc., vol. 68, pp. 751 to 753 (1946).
Quelet et al., Chemical Abstracts, vol. 55, cols. 3534a,d (1961).
Shankar et al., Chemical Abstracts, vol. 97, #127148n (1982).
Streitwieser al., I, J. Amer. Chem. Soc., vol. 85, pp. 1757 to 1761 (1963).
Streitwieser et al., II, J. Amer. Chem. Soc., vol. 86, pp. 4938 to 4942 (1964).
Baker et al., J. Chem. Soc. (C), 1605-1606 (1969).
Beard et al., J. Org. Chem., 38, 3673-3677 (1973).
Brasen and Hauser, Org. Syn. Coll., vol. IV, 582-584 (1963).
Collins, et al., Tet. Letters, 3363-3366 (1968).
Crossland et al., J. Am. Chem. Soc., 93, 4217-4219 (1971).
DeChristopher et al., J. Am. Chem. Soc., 91, 2384-2385 (1969).
Finch and Schlittler, Tetrahedron, 24, 5421-5424 (1968).
Gruntz, et al., J.C.S. Chem. Comm., 701 (1977).
Hartman and Rahrs, Org. Syn. Coll., vol. III, pp. 650-652 (1955).
Kirmse, Angew, Chem. Int. Ed. Engl., 15, 251-261 (1976).
March, I , "Advance Organic Chemistry," McGraw-Hill, 1977, p. 322 et seq.
March, II, loc. cit., pp. 227-230.
Meyer et al., Chem. Ber., 103, 37-45 (1970).
Morrison and Boyd, "Organic Chemistry," 2nd Ed., Allyn and Bacon, Inc., Boston, 1971, pp. 916-918.
Overberger and Anselme, J. Am. Chem. Soc., 86, 658-660 (1964).
Sheehan and Bolhofer, J. Am. Chem. Soc., 72, 2786-2788 (1950).
Subramanian, et al., Synthesis, 293-294 (1973).
Szeja, Synthesis, 822-823 (1979).
Williams and Halpern, Synthesis, 727-728 (1974).
Winberg and Fawcett, Org. Syn. Coll., vol. V., 883-886 (1973).

Primary Examiner—FLoyd D. Higel
Attorney, Agent, or Firm—Richard L. Hansen; H. Robinson Ertelt

[57] ABSTRACT

A 2,2'-bridged[1,1'-biphenyl]-3-ylmethyl compound of the following formula is an intermediate to insecticidal esters.

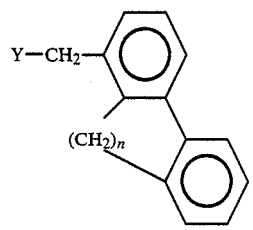

wherein n is 1–4 and Y is a leaving group readily displaced by carboxylate anions.

21 Claims, No Drawings

[1,1'-BIPHENYL]COMPOUNDS HAVING A 2,2'-(ALKYL)BRIDGE AND A 3-YL(SUBSTITUTED)METHYL SUBSTITUENT

This application is a continuation in part of application Ser. No. 331,506, filed Dec. 17, 1981, now U.S. Pat. No. 4,433,182, which is a division of application Ser. No. 259,111, filed Apr. 30, 1981, now abandoned.

This invention pertains to the field of carboxylic acid esters which are pyrethroid insecticides, more specifically processes and intermediates thereto.

Pyrethrins have long been of interest as insecticides. Ever since it was discovered that pyrethrins are organic esters, various synthetic modifications have been made in the carboxylic acid and in the alcohol moieties on either side of the ester linkage. Many of the synthetic pyrethroids are more effective than the natural pyrethrins, and recent modifications have overcome a chronic pyrethrin problem—instability to air and light.

The carboxylic acid moiety in the aforesaid esters is often a 2,2-dimethylcyclopropane-1-carboxylic acid with various substituents in the 3-position. Many variations in the alcohol moiety of the aforesaid esters have been investigated also. For example, it has been found that insecticidal and acaricidal esters result when a 2,2'-bridged[1,1'-biphenyl]-3-ylmethyl alcohol moiety is coupled with certain carboxylic acid moieties as disclosed in U.S. Pat. No. 4,433,182, which is incorporated herein by reference.

The active 2,2'-bridged[1,1'-biphenyl]-3-ylmethyl esters are prepared by reaction between a carbonyl halide, e.g., a chloride, RCOCl, wherein R is a suitable acid residue as disclosed in U.S. Pat. No. 4,433,182, for example; an acid, RCOOH; an ester, RCOOR', wherein R' is conveniently a $C_1$-$C_6$ alkyl group; an anhydride, RCOOR", wherein R" is $C_1$-$C_6$ alkylcarbonyl, or aryl sulfonyl; or a nitrile, RCN, and an appropriate 2,2'-bridged[1,1'-biphenyl]-3-ylmethanol.

Alternatively, the esters are prepared by nucleophilic substitution, i.e., reacting an acid or acid salt, RCOOM, wherein R is as defined above, and M is an alkali or alkaline earth metal, e.g., Li, Na, K, Ca, or Mg; a transition metal, e.g., Ag; or ammonium, or alkyl-substituted ammonium, with a 2,2'-bridged[1,1'-biphenyl]-3-ylmethyl compound wherein the benzylic carbon atom carries a "leaving group" which is readily displaced by carboxylate anions. 2,2'-Bridged[1,1'-biphenyl]-3-ylmethyl compounds carrying such leaving groups are the subject of this application and are described by the structural formula

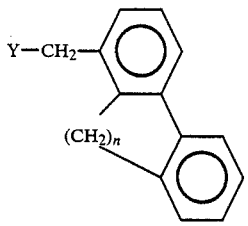

wherein n is 1-4 and Y is a leaving group readily displaced by carboxylate anions.

Preparation of the corresponding 2,2'-bridged[1,1'-biphenyl]-3-ylmethyl alcohols is disclosed in U.S. Pat. No. 4,433,182. A 2,2'-bridged[1,1'-biphenyl]-3-ylmethyl alcohol can be converted into the corresponding 2,2'-bridged[1,1'-biphenyl]-3-ylmethyl bromide by treating a solution of the alcohol in ether with phosphorous tribromide or phosphorous pentabromide. Similarly, a 2,2'-bridged[1,1-biphenyl]-3-ylmethyl bromide can be converted into the corresponding alcohol by first treating the bromide with sodium acetate in acetic acid and then treating the thus produced biphenyl acetate with sodium hydroxide in methanol. These techniques are available in the prior art.

Suitable leaving groups Y in the aforesaid structural formula are known in the art today and include, e.g., bromo, chloro, (methylsulfonyl)oxy, and (4-methylbenzenesulfonyl)oxy. It is expected that additional leaving groups readily displaced by carboxylate anions will be discovered in the future. The instant invention contemplates these future developments. It is recognized that any leaving groups readily displaced by carboxylate anions are and will be functional equivalents for Y in the aforesaid structural formula for the 2,2'-bridged[1,1'-biphenyl]-3-ylmethyl compounds of this invention.

In order that a leaving group Y will be readily displaced by a carboxylate anion, the anion of the leaving group should be a poorer nucleophile, generally a weaker base, than the carboxylate anion. The relationship between nucleophilicity and basicity is set forth in March, "Advanced Organic Chemistry," McGraw-Hill, 1977, p. 322 et seq. In other words, to a reasonable approximation, the conjugate acid of the leaving group anion should have a $pK_a$ which is less than that of the conjugate carboxylic acid. The $pK_a$'s for a large number of acids are known; e.g., see March, loc. cit., pp. 227-230, and the $pK_a$'s of the conjugate acids of leaving group anions which are now or later become candidates for Y in the aforesaid structural formula can by measured by methods known to those skilled in the art. In general, a 2,2'-bridged[1,1'-biphenyl]-3-ylmethyl compound carrying a desired leaving group can be prepared by nucleophilic displacement on the corresponding compound carrying a leaving group whose anion is a weaker base than the anion of the desired leaving group.

Suitable leaving groups Y include halo, especially chloro and bromo. The terms "halo" or "halogen" employed herein mean fluorine, chlorine or bromine. In general, a 2,2'-bridged[1,1'-biphenyl]-3-ylmethyl chloride is prepared by chlorination of the corresponding 3-methyl compound with N-chlorosuccinimide, with thionyl chloride, chlorine under irradiation, or with sulfonyl chloride and a peroxide such as benzoyl peroxide, or by treating the corresponding 2,2'-bridged[1,1'-biphenyl]-3-ylmethanol with thionyl chloride. Reaction of 2,2'-bridged[1,1'-biphenyl]-3-ylmethyl compounds carrying halo leaving groups with suitable carboxylates to produce insecticidal esters is described in U.S. Pat. No. 4,214,004 and more generally by Hartman and Rahrs, *Org. Syn.*, Coll. Vol. III, pp. 650-652 (1955), as well as by Finch and Schlittler, *Tetrahedron*, 24, 5421-5424 (1968). Specific 2,2'-bridged[1,1'-biphenyl]-3-ylmethyl compounds in which Y is halo include, for example, 1-chloromethyl-9,10-dihydrophenanthrene, 4-chloromethyl-6,7-dihydro-5H-dibenzo[a,c]cycloheptene, 4-chloromethyl-5,6,7,8-tetrahydrodibenzo[a,c]cyclooctene, 1-bromomethyl-9,10-dihydrophenanthrene, 4-bromomethyl-6,7-dihydro-5H-dibenzo[a,c]cycloheptene, and 4-bromomethyl-5,6,7,8-tetrahydrodibenzo[a,c]cyclooctene.

Sulfonyloxy constitutes another suitable type of leaving group Y, e.g., aromatic sulfonyloxy groups of the formula

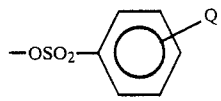

in which the specific ring position substituted by Q and the identity of Q are selected to optimize the $pK_a$ of the conjugate sulfonic acid of the formula

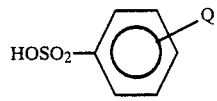

according to the principles described above. Specific leaving groups within this structural representation include those in which Q is selected from hydrogen, lower alkyl (straight or branched chain), lower alkyl substituted with one or more halogen atoms, halogen, or nitro. Where employed herein the term "lower" modifying "alkyl" means $C_1$-$C_6$, preferably $C_1$-$C_4$. More specifically, examples include (benzenesulfonyl)oxy; (methylbenzenesulfonyl)oxy, especially (4-methylbenzenesulfonyl)oxy; (bromobenzenesulfonyl)oxy, especially (4-bromobenzenesulfonyl)oxy; and (nitrobenzenesulfonyl)oxy, especially (4-nitrobenzenesulfonyl)oxy. Preparation of 2,2'-bridged[1,1'-biphenyl]-3-ylmethyl compounds having the (4-methylbenzenesulfonyl)oxy leaving group can be accomplished by treating the corresponding 3-ylmethanols with (4-methyl)benzenesulfonyl chloride. 2,2'-Bridged[1,1'-biphenyl]-3-ylmethyl compounds with other leaving groups of this type can be prepared by the same general method, substituting the appropriate sulfonyl chloride, all as described by Szeja, Synthesis, 822–823 (1979) The procedure described by Baker, et al., J. Chem. Soc. (C), 1605–1606 (1969), can be employed when reacting 2,2'-bridged[1,1'-biphenyl]-3-ylmethyl compounds carrying such sulfonyloxy leaving groups with suitable carboxylates. Specific 2,2'-bridged[1,1'-biphenyl]-3-ylmethyl compounds in which Y is an aromatic sulfonyloxy group include, for example, (9,10-dihydro-1-phenanthryl)methyl 4-methylbenzenesulfonate, (6,7-dihydro-5H-dibenzo[a,c]cyclohepten-4-yl)methyl 4-methylbenzenesulfonate, (5,6,7,8-tetrahydrodibenzo[a,c]cycloocten-4-yl)methyl 4-methylbenzenesulfonate, (9,10-dihydro-1-phenanthryl)methyl 4-bromobenzenesulfonate, (6,7-dihydro-5H-dibenzo[a,c]cyclohepten-4-yl)methyl 4-bromobenzenesulfonate, (5,6,7,8-tetrahydrodibenzo[a,c]cycloocten-4-yl)methyl 4-bromobenzenesulfonate, (9,10-dihydro-1-phenanthryl)methyl 4-chlorobenzenesulfonate, (6,7-dihydro-5H-dibenzo[a,c]cyclohepten-4-yl)methyl 4-chlorobenzenesulfonate, and (5,6,7,8-tetrahydrodibenzo[a,c]cycloocten-4-yl)methyl 4-chlorobenzenesulfonate.

Closely related alkyl or fluoroalkyl sulfonyloxy substituents, which are also suitable leaving groups Y, are described by the formula

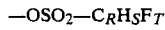

in which R is 1–6, and S+T is 3–13, while S and T are independently 0–13, selected to optimize the $pK_a$ of the conjugate sulfonic acid according to the principles set forth above. Examples of such leaving groups include (alkylsulfonyl)oxy in which T=0, especially lower (alkylsulfonyl)oxy, a specific example being (methanesulfonyl)oxy, in which R=1, S=3 and T=0. 2,2'-Bridged[1,1'-biphenyl]-3-ylmethyl compounds carrying this leaving group are prepared by treating the corresponding 3-ylmethanol with methanesulfonyl chloride. 2,2'-Bridged[1,1'-biphenyl]-3-ylmethyl compounds with other leaving groups of this type are similarly prepared using the appropriate sulfonyl chloride as described by Meyer, et al., Chem. Ber., 103, 37–45 (1970) and by Szeja, loc. cit. The former reference also describes displacement of the (methanesulfonyl)oxy group with carboxylate, and that description is applicable to other (alkylsulfonyl)oxy leaving groups as well. Specific 2,2'-bridged[1,1'-biphenyl]-3-ylmethyl compounds in which Y is an (alkylsulfonyl)oxy substituent include, for example, (9,10-dihydro-1-phenanthryl)methyl methanesulfonate, (6,7-dihydro-5H-dibenzo[a,c]cyclohepten-4-yl)methyl methanesulfonate, and (5,6,7,8-tetrahydrodibenzo[a,c]cycloocten-4-yl)methyl methanesulfonate.

Other useful leaving groups Y of the aforesaid formula are those containing fluorine substituents, i.e., fluoroalkyl. A specific example is the (2,2,2-trifluoroethanesulfonyl)oxy group, with R=2, S=2 and T=3. 2,2'-Bridged[1,1'-biphenyl]-3-ylmethyl compounds carrying the (2,2,2-trifluoroethanesulfonyl)oxy leaving group are prepared from the corresponding 3-ylmethanols by the procedure described by Crossland, et al., J. Am Chem. Soc., 93, 4217–4219 (1971). Structurally similar are the trifluoromethanesulfonyl (R=1, S=0, T=3) and nonafluorobutylsulfonyl (R=4, S32 0, T=9) leaving groups. Preparation from the corresponding 3-ylmethanols of 2,2'-bridged[1,1'-biphenyl]-3-ylmethyl compounds carrying the former leaving group can be carried out as described by Beard, et al., J. Org. Chem., 38, 3673–3677 (1973), compounds with the latter leaving group by the method of Subramanian, et al., Synthesis, 293–294 (1973). 2,2'-Bridged[1,1'-biphenyl]-3-ylmethylcompounds with other fluoroalkyl sulfonyl leaving groups are similarly prepared. Reaction of the (fluoroalkylsulfonyl)oxy sulfonyl carrying compounds with suitable carboxylates can be effected by the method of Meyer, et al., loc. cit. Specific 2,2'-bridged[1,1'-biphenyl]-3-ylmethyl compounds in which the leaving group Y is fluoroalkyl include, for example, (9,10-dihydro-1-phenanthryl)methyl(2,2,2-trifluoroethanesulfonyl)oxy, (6,7-dihydro-5H-dibenzo[a,c]cyclohepten-4-yl)methyl 2,22-trifluoroethanesulfonate, (5,6,7,8-tetrahydrodibenzo[a,c]cycloocten-4-yl)methyl (2,2,2-trifluoroethanesulfonyl)oxy, (9,10-dihydro-1-phenanthryl)methyl trifluoromethanesulfonate, (6,7-dihydro-5H-dibenzo[a,c]cyclohepten-4-yl)methyl trifluoromethanesulfonate, and (5,6,7,8-tetrahydrodibenzo[a,c]cycloocten-4-yl)methyl trifluoromethanesulfonate.

Several leaving groups in which nitrogen is bonded to the 3-ylmethyl group are also suitable as Y. 2,2'-Bridged[1,1'-biphenyl]-3-ylmethyl compounds carrying these leaving groups are often obtainable from the corresponding 3-ylmethanamines. The latter can be made from the corresponding 3-ylmethyl bromides by the Gabriel synthesis, the details of which are described by Sheehan and Bolhofer, J. Am. Chem. Soc., 72, 2786-88 (1950) and more generally in Morrison and Boyd, "Organic Chemistry," 2nd Ed., Allyn and Bacon, Inc., Boston, 1971, pp. 916–918. For example, (9,10-dihydro- 1-phenanthryl)methanamine results as follows, and other 2,2′-bridged[1,1′-biphenyl]-3-ylmethanamines are made similarly.

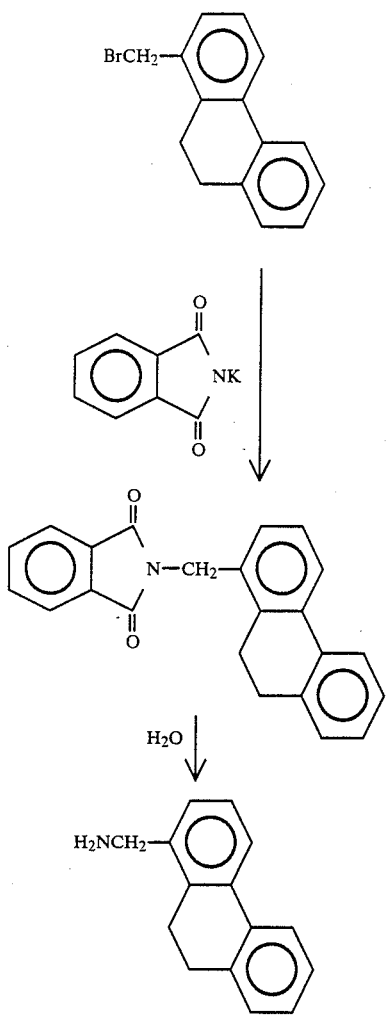

These nitrogen-containing leaving groups include quaternary ammonium of the formula

in which $R_1$, $R_2$ and $R_3$ are hydrocarbon groups, e.g., independently lower alkyl or phenyl, and $X^-$ is a suitable anion, such as hydroxide, bromide or iodide, all selected to optimize the $pK_a$ of the corresponding conjugate acid as described above. Specific examples include N,N-dimethylbenzenaminium hydroxide and N,N-dimethylmethanaminium bromide. Preparation of 2,2′-bridged[1,1′-biphenyl]-3-ylmethyl compounds with N,N-dimethylbenzenaminium chloride as the leaving group Y from the corresponding 3-ylmethyl chloride, as well as the subsequent reaction thereof with carboxylate can be effected as described by Williams and Halpern, *Synthesis*, 727–728 (1974). 2,2′-Bridged-[1,1′-biphenyl]-3-ylmethyl compounds with N,N-dimethylmethanaminium salts as leaving groups are prepared from the corresponding 3-ylmethyl bromides by the method described by Winberg and Fawcett, *Org. Syn., Coll.* Vol. V., 883–886 (1973); the displacement with carboxylate can be conducted as described by Brasen and Hauser, *Org. Syn., Coll.* Vol. IV., 582–584 (1963).

2,2′-Bridged[1,1′-biphenyl]-3-ylmethyl compounds carrying other quaternary ammonium leaving groups are prepared and reacted with suitable carboxylates by similar techniques. 2,2′-Bridged-[1,1′-biphenyl]-3-ylmethyl compounds in which the leaving group Y is quaternary ammonium include, for example, N,N,1-trimethyl-N-phenyl(9,10-dihydrophenanthryl)aminium hydroxide, N,N,4-trimethyl-N-phenyl(6,7-dihydro-5H-dibenzo[a,c]cycloheptenyl)aminium hydroxide, N,N,4-trimethyl-N-phenyl(5,6,7,8-tetrahydrodibenzo[a,c]cyclooctenyl)aminium hydroxide, N,N,N,1-tetramethyl(9,10-dihydrophenanthryl)aminium bromide, N,N,N,4-tetramethyl(6,7-dihydro-5H-dibenzo[a,c]cycloheptenyl)aminium bromide, and N,N,N,4-tetramethyl(5,6,7,8-tetrahydrodibenzo[a,c]cyclooctenyl)aminium bromide.

Additional nitrogen-containing leaving groups suitable as Y are sulfonamido, e.g., aromatic sulfonamido described by the formula

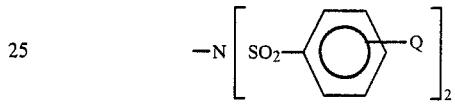

in which the ring position substituted by Q and the specific nature of Q are chosen to optimize the $pK_a$ of the conjugate acid

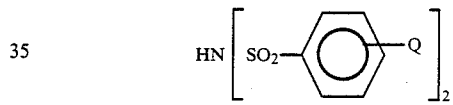

according to the principles set forth above. Specific leaving groups of this type include those in which Q is selected from hydrogen, lower alkyl (straight or branched chain), lower alkyl substituted with one or more halogen atoms, halogen, or nitro. More specifically, examples of such leaving groups include N-(4-methylbenzenesulfonyl)-4-methylbenzenesulfonamido and N-(4-nitrobenzenesulfonyl)-4-nitrobenzenesulfonamido. Preparation of 2,2′-bridged[1,1′-biphenyl]-3-ylmethyl compounds with such leaving groups from the corresponding 3-ylmethanamines may be accomplished by the method of Dechristopher, et al., *J. Am. Chem. Soc.*, 91, 2384–2385 (1969). Reaction of the resultant 2,2′-bridged[1,1′-biphenyl]-3-ylmethyl compounds with suitable carboxylates can be effected by the same method employed for 4-methylbenzenesulfonates, i.e., see Baker, et al. loc. cit. 2,2′-Bridged[1,1′-biphenyl]-3-ylmethyl compounds carrying aromatic sulfonamide leaving groups include, for example,N-(9,10-dihydro-1-phenanthryl)methyl-N-(4-nitrobenzenesulfonyl)-4-nitrobenzenesulfonamide, N-(6,7-dihydro-5H-dibenzo[a,c]cyclohepten-4-yl)methyl-N-(4-nitrobenzenesulfonyl)-4-nitrobenzenesulfonamide, and N-(5,6,7,8-tetrahydrodibenzo[a,c]cycloocten-4-yl)methyl-N-(4-nitrobenzenesulfonyl)-4-nitrobenzenesulfonamide.

Other useful nitrogen containing leaving groups Y include the pyridinium group, e.g., 1-(2,4,6-triphenylpyridinium),

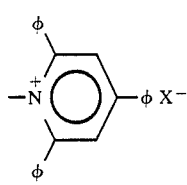

where $X^-$ is an anion such as tetrafluoroborate. 2,2'-Bridged-[1,1'-biphenyl]-3-ylmethyl compounds with such leaving groups can be prepared from the corresponding 3-ylmethanamines by the procedure described by Gruntz, et al., *Chem. Commun.*, 701 (1977). The resultant 2,2'-bridged[1,1'-biphenyl]-3-ylmethyl compounds can be reacted with suitable carboxylates by the process described in the same reference. 2,2'-Bridged[1,1'-biphenyl]-3-ylmethyl compounds with pyridinium as the leaving group Y include, for example, (9,10-dihydro-1-phenanthryl)methyl 2,4,6-triphenylpyridinium tetrafluoroborate, (6,7-dihydro-5H-dibenzo[a,c]cyclohepten-4-yl)methyl 2,4,6-triphenylpyridinium tetrafluoroborate, and (5,6,7,8-tetrahydrodibenzo[a,c]cycloocten-4-yl)methyl 2,4,6-triphenylpyridinium tetrafluoroborate.

Diazo is another useful leaving group Y. 2,2'-Bridged-[1,1'-biphenyl]-3-ylmethyl compounds carrying diazo as the leaving group can be prepared from the corresponding 3-ylmethanols via the aldehydes using the procedure described by Collins, et al., *Tet. Letters*, 3363–3366 (1968), followed by that of Overberger and Anselme, *J. Am. Chem. Soc.*, 86, 658–660 (1964). For example, (9,10-dihydro-1-phenanthyl)methyl diazomethane can be prepared by the following sequence of reactions.

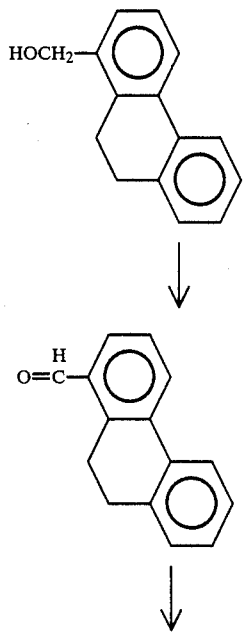

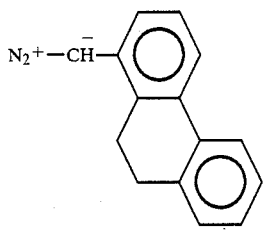

The resultant diazomethane can be reacted with an appropriate carboxylic acid, producing an ester, according to the procedure of Kirmse, *Angew. Chem. Int. Ed. Engl.*, 15, 251–261 (1976).

The invention is not limited to 2,2'-bridged[1,1'-biphenyl]-3-ylmethyl compounds in which the leaving group Y is restricted to the specific substituents recited above. The recitation is by way of exemplification only. Many other functionally suitable substituents are now well known in the art and more are expected to become known in the future, both as to preparing 2,2'-bridged-[1,1'-biphenyl]-3-ylmethyl compounds carrying those substituents as well as reacting the resultant 2,2'-bridged[1,1'-biphenyl]-3-ylmethyl compounds in nucleophilic displacement of those substituents with suitable acids or acid salts. As to leaving group Y, this invention contemplates function, rather than specific structure. Guidance in selecting appropriate structure to achieve that function is provided above.

I claim:

1. A 2,2'-Bridged[1,1'-biphenyl]-3-ylmethyl compund of the formula

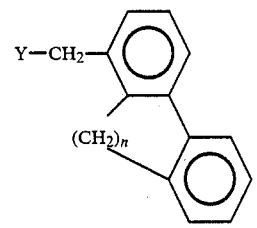

wherein n is 2–4, and Y is a leaving group readily displaced by carboxylate anions.

2. A compound of claim 1 wherein Y is an aromatic sulfonyloxy group of the formula

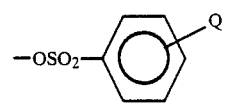

in which Q is selected from hydrogen, lower alkyl (straight or branched chain), lower alkyl substituted with one or more halogen atoms, halogen, or nitro.

3. A compound of claim 2 wherein said aromatic sulfonyloxy group is selected from (benzenesulfonyl)oxy, (methylbenzenesulfonyl)oxy, (bromobenzenesulfonyl)oxy, and (nitrobenzenesulfonyl)oxy.

4. A compound of claim 1 wherein Y is an alkyl or fluoroalkyl sulfonyloxy substituent of the formula

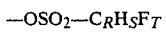

in which R is 1–6, S+T is 3–13, and S and T are independently 0–13.

5. A compound of claim 4 wherein said sulfonyloxy substituent is selected from (methylsulfonyl)oxy, (2,2,2-trifluoroethanesulfonyl)oxy, and (nonafluorobutylsulfonyl)oxy.

6. A compound of claim 1 wherein Y is a quaternary ammonium group of the formula $$-NR_1R_2R_3{}^+X^-$$

in which $R_1$, $R_2$ and $R_3$ are hydrocarbon groups and $X^-$ is an anion.

7. A compound of claim 6 wherein said quaternary ammonium group is selected from N,N-dimethylbenzenaminium hydroxide and N,N-dimethylmethanaminium bromide.

8. A compound of claim 1 wherein Y is an aromatic sulfonamido group of the formula

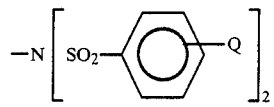

in which Q is selected from hydrogen, lower alkyl (straight or branched chain), lower alkyl substituted with one or more halogen atoms, halogen, and nitro.

9. A compound of claim 8 wherein said sulfonamido group is selected from N-(4-methylbenzenesulfonyl)-4-methylbenzenesulfonamido and N-(4-nitrobenzenesulfonyl)-4-nitrobenzenesulfonamido.

10. A compound of claim 1 wherein Y is 1-(2,4,6-triphenylpyridinium)tetrafluoroborate.

11. A compound of claim 1 wherein Y is diazomethyl.

12. A compound of claim 1 wherein Y is halo.

13. A compound of claim 12 wherein halo is selected from chlorine and bromine.

14. A compound of claim 13 selected from 1-chloromethyl-9,10-dihydrophenanthrene, 4-chloromethyl-6,7-dihydro-5H-dibenzo[a,c]cycloheptene, 4-chloromethyl-5,6,7,8-tetrahydrodibenzo[a,c]cyclooctene, 1-bromomethyl-9,10-dihydrophenanthrene, 4-bromomethyl-6,7-dihydro-5H-dibenzo[a,c]cycloheptene, and 4-bromomethyl-5,6,7,8-tetrahydrodibenzo[a,c]cyclooctene.

15. A compound of claim 2 selected from (9,10-dihydro-1-phenanthryl)methyl 4-methylbenzenesulfonate, (6,7-dihydro-5H-dibenzo[a,c]cyclohepten-4-yl)methyl 4-methylbenzenesulfonate, (5,6,7,8-tetrahydrodibenzo[a,c]cycloocten-4-yl)methyl 4-methylbenzenesulfonate, (9,10-dihydro-1-phenanthryl)methyl 4-bromobenzenesulfonate, (6,7-dihydro-5H-dibenzo[a,c]cyclohepten-4-yl)methyl 4-bromobenzenesulfonate, (5,6,7,8-tetrahydrodibenzo[a,c]cycloocten-4yl)methyl 4-bromobenzenesulfonate, (9,10-dihydro-1-phenanthryl)methyl 4-chlorobenzenesulfonate, (6,7-dihydro-5H-dibenzo[a,c]cyclohepten-4yl)methyl 4-chlorobenzenesulfonate, and (5,6,7,8-tetrahydrodibenzo[a,c]cycloocten-4-yl)methyl 4-chlorobenzenesulfonate.

16. A compound of claim 4 selected from (9,10-dihydro-1-phenanthryl)methyl methanesulfonate, (6,7-dihydro-5H-dibenzo[a,c]cyclohepten-4-yl)methyl methanesulfonate, and (5,6,7,8-tetrahydrodibenzo[a,c]cycloocten-4-yl)methyl methanesulfonate.

17. A compound of claim 4 selected from (9,10-dihydro-1-phenanthryl)methyl 2,2,2-trifluoroethanesulfonate, (6,7-dihydro-5H-dibenzo[a,c]cyclohepten-4-yl)methyl 2,2,2-trifluoroethanesulfonate, (5,6,7,8-tetrahydrodibenzo[a,c]cycloocten-4-yl)methyl 2,2,2-trifluoroethanesulfonate, (9,10-dihydro-1-phenanthryl)methyl trifluoromethanesulfonate, (6,7-dihydro-5H-dibenzo[a,c]cyclohepten-4-yl)methyl trifluoromethanesulfonate, and (5,6,7,8-tetrahydrodibenzo[a,c]cycloocten-4-yl)methyl trifluoromethanesulfonate.

18. A compound of claim 6 selected from N,N,1-trimethyl-N-phenyl(9,10-dihydrophenanthryl)aminium hydroxide, N,N,4-trimethyl-N-phenyl(6,7-dihydro-5H-dibenzo[a,c]cycloheptenyl)aminium hydroxide, N,N,4-trimethyl-N-phenyl(5,6,7,8-tetrahydrodibenzo[a,c]cyclooctenyl)aminium hydroxide, N,N,N,1-tetramethyl(9,10-dihydrophenanthryl)aminium bromide, N,N,N,4-tetramethyl(6,7-dihydro-5H-dibenzo[a,c]cycloheptenyl)aminium bromide, and N,N,N,4-tetramethyl(5,6,7,8-tetrahydrodibenzo[a,c]cyclooctenyl)aminium bromide.

19. A compound of claim 8 selected from N-(9,10-dihydro-1-phenanthryl)methyl-N-(4-nitrobenzenesulfonyl)-4-nitrobenzenesulfonamide, N-(6,7-dihydro-5H-dibenzo[a,c]cyclohepten-4-yl)methyl-N-(4-nitrobenzenesulfonyl)-4-nitrobenzenesulfonamide, and N-(5,6,7,8-tetrahydrodibenzo[a,c]cycloocten-4-yl)methyl-N-(4-nitrobenzenesulfonyl)-4-nitrobenzenesulfonamide.

20. A compound of claim 10 selected from (9,10-dihydro-1-phenanthryl)methyl 2,4,6-triphenylpyridinium tetrafluoroborate, (6,7-dihydro-5H-dibenzo[a,c]cyclohepten-4-yl)methyl 2,4,6-triphenylpyridinium tetrafluoroborate, and (5,6,7,8-tetrahydrodibenzo[a,c]cycloocten-4-yl)methyl 2,4,6-triphenylpyridinium tetrafluoroborate.

21. (9,10-Dihydro-1-phenanthryl)methyl diazomethane, a compound of claim 11.

* * * * *